United States Patent [19]

Papritz et al.

[11] Patent Number: 5,016,854
[45] Date of Patent: May 21, 1991

[54] HEIGHT ADJUSTABLE SUPPORTING DEVICE FOR AN INSTRUMENT

[75] Inventors: Franz Papritz; Hansruedi Widmer, both of Niederscherli, Switzerland

[73] Assignee: Haag-Streit AG, Liebefeld, Switzerland

[21] Appl. No.: 362,812

[22] Filed: Jun. 7, 1989

[30] Foreign Application Priority Data

Jun. 16, 1988 [CH] Switzerland .................. 2333/88

[51] Int. Cl.$^5$ ............................................. F16M 13/00
[52] U.S. Cl. ................................. 248/563; 248/669; 248/162.1
[58] Field of Search ............ 248/561, 566, 563, 576, 248/577, 578, 599, 600, 601, 648, 669, 162.1, 157, 419, 177, 178; 108/144, 147, 146; 29/227, 229; 267/175, 177, 169

[56] References Cited

U.S. PATENT DOCUMENTS

| 1,389,657 | 9/1921 | Harsley | 29/227 |
| 1,880,280 | 10/1932 | Replogle | 248/563 |
| 2,174,209 | 9/1939 | Genest | 248/561 |
| 2,729,273 | 1/1956 | Hamilton | 248/576 |
| 3,463,579 | 8/1969 | Papritz | |
| 3,912,248 | 10/1975 | Pickford | 248/600 |
| 4,116,548 | 9/1978 | Persson | |

FOREIGN PATENT DOCUMENTS

| 0143134 | 11/1983 | European Pat. Off. |
| 2307044 | 8/1974 | Fed. Rep. of Germany |
| 41438 | 10/1932 | France | 248/561 |

Primary Examiner—Alvin C. Chin-Shue
Assistant Examiner—Robert A. Olson
Attorney, Agent, or Firm—Marks, Murase & White

[57] ABSTRACT

A spring is continuously acting on an upper part adjustable in the height by a spindle for compensating the weight of the vertical adjustable parts. An additional compensating spring acts over a piston on the upper part. By means of a screw which can be screwed in a threaded hole, the piston can be coupled with the base which is not displaceable in the height so that the effect of the additional spring is cut off. Many compensating springs can be provided which, at choice, can be rendered effective or ineffective in order to compensate for different weights.

14 Claims, 1 Drawing Sheet

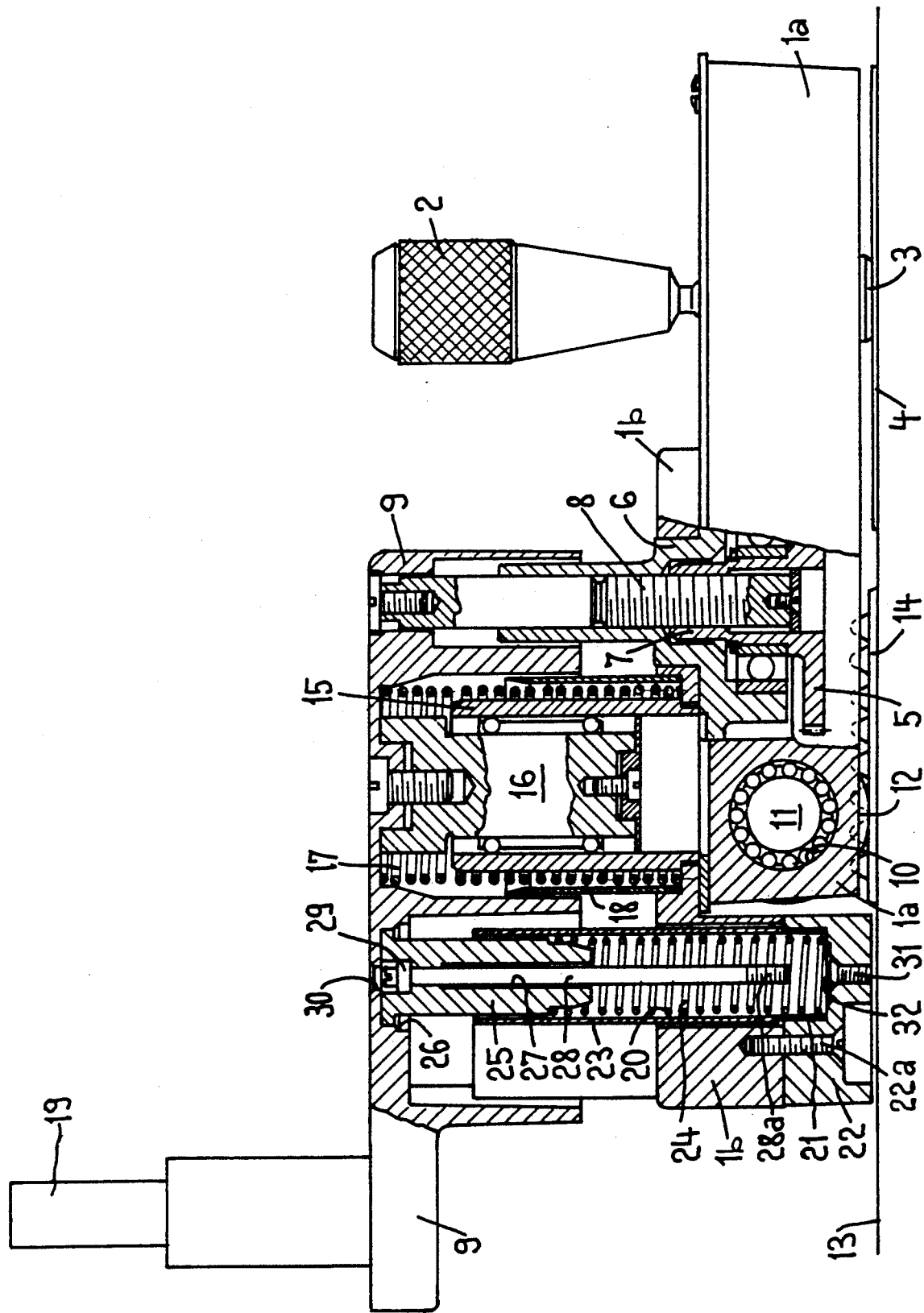

HEIGHT ADJUSTABLE SUPPORTING DEVICE FOR AN INSTRUMENT

BACKGROUND OF THE INVENTION

The present invention relates to a height adjustable supporting device for an instrument, more particularly an ophthalmological instrument, whereby the weight of the instrument and of the height adjustable parts of the supporting device are compensated by spring force. Known devices of this kind are provided with a compensating spring which is adjusted to a determined weight (U.S. Pat. No. 3,463,579). However, the weight to compensate is in many cases not given one for all in that either instruments of different types are used or in that instruments with a determined basic execution may be combined with different accessories. As an example, the microscope of a slit lamp can be completed with different accessories, e.g. a tonometer, a changer of stereo angle, a beam splitter, a secondary viewing tube and other aggregates. However, a unique compensating spring can compensate satisfactorily only a determined weight and a bad weight, compensation renders more difficult the vertical adjustment of the supporting device, resp. of the instrument supported by it.

SUMMARY OF THE INVENTION

It is an object of the present invention to achieve in a simple way the gradation of the compensating force, in order to optimally compensate for the weights of different instruments. The solution of this problem, in accordance with the present invention is that at least one additional compensating spring is capable to be rendered effective or ineffective, by the fact that its extremities can be coupled together, resp. uncoupled from each other. Thus, the number and the force of the compensating springs can be varied in order to achieve a gradation adapted to the situation of the whole compensating effect. Preferably, each compensating spring is traversed by an anchoring element, e.g. a tie bolt which can be coupled, e.g. screwed to the base. The switching on and off, resp. the coupling, resp. uncoupling of the additional compensating springs can be achieved in a very simple manner, e.g. by means of a screw-driver. It is however also possible to provide means for coupling and uncoupling which can be actuated without any tool.

The invention will be further explained by means of an example of execution illustrated in the drawing.

BRIEF DESCRIPTION OF THE DRAWING

The unique FIGURE shows a vertical section, partly in plane view of this example of execution.

DESCRIPTION OF THE PREFERRED EMBODIMENT

The supporting device comprises a base 1 consisting of the parts 1a and 1b. Part 1a is provided with a precise adjustment lever 2 slewably and pivotably mounted. The lower end of this lever engages into a plate 3 which is supported on a slideway lining 4. By slewing of the lever 2, the base 1 can be finely adjusted in the horizontal plane with respect to the plate 3. A rotation of the lever 2 about its axis is transmitted to a toothed wheel 5 which is mounted in a bearing bush 6 fixedly connected to the part 1b and which is in one piece with a spindle nut 7. In this spindle nut 7 is engaged a spindle 8 which is guided in the bearing bush 6 in order to be vertically displaceable, the upper end of the spindle 8 being connected with a vertically mobile upper part 9 of the supporting device. Hence, any rotation of the lever 2 is transmitted through the toothed wheel 5 to the spindle nut 7 and it causes through the spindle 8 a fine adjustment in the vertical direction of the upper part 9. Such a device for a fine adjustment is described in the above mentioned U.S. Pat. No. 3,463,579 and it does not require any further explanation.

A shaft 11 is mounted by means of a ball bearing in a cross hole 10 of the part 1a. At both ends of this shaft 11, projecting from the part 1a, are fastened supporting wheels 12 the rims of which, provided with holes, engaging each in a toothed rail 14 fastened on the table 13 of the instrument. Both wheels 12 and the plate 3 thus provide for a three point support for the base 1. The base can be roughly adjusted horizontally in a determined region, whereby the plate 3 slides on the coating 4, the wheels 12 roll on the toothed rails 14 such that they retain the base in a determined orientation and in that the base can be cross shifted on the shaft 11.

In part 1b of the base 1 is fastened a bearing bush 15 in which a guiding cog 16 is vertically engaged through a ball bearing. The cog 16 is fixedly connected with the upper part 9 so that it serves for the precise vertical guiding of this upper part. The bearing bush 15 and the guiding cog 16 are surrounded by a pressure spring 17 acting between the base 1 and the upper part 9 so that it serves for the weight compensation of the vertically mobile part of the supporting device and of an instrument supported thereon. The compensating spring 17 is guided in its lower part in a bushing 18. The FIGURE shows a view of a bearing neck 19 connected to the upper part 9, the swivel arm of a microscope of a split lamp being e.g. mounted at the lower part of this bearing neck and the lighting unit of the split lamp being slewably mounted at the upper part of the bearing neck 19.

In one or more holes 20 of the part 1b of the base 1, resp. in holes 21 of a plate 22 removably connected to the base 1b by means of one or more screws 22a is arranged a bushing 23 which contains an additional compensating spring 24. This additional compensating spring is supported at the bottom of the hole 21 and it acts at the top on a piston 25 vertically displaceable in the bushing 23, the upper part of the piston being loosely engaged in a recess 26 of the upper part 9. In a traversing hole 27 of the piston 25 is provided a screw 28, the head 29 of which being supported in an enlarged, upper part of the hole 27. The slit of the screw 28 can be attained through an opening 30 in the upper part 9. The device is illustrated in a middle position, that is the upper part 9 is neither in its uppermost nor in its lowermost position. The lower part 28a of the screw 28 is provided with a thread and it is in a determined distance from a threaded hole 31 coaxial to the screw 28, in the plate 22. Over the threaded hole 31 is provided a guiding cone 32 which serves to guide the lower part 28a provided with a thread of the screw 28 coaxially over the threaded hole 31 when the screw is lowered down to the threaded hole. While the FIGURE only shows one additional compensating spring 24 with the associated elements, many such springs can be arranged either in a row, side by side, in a ring or in a polygon in order to render possible different gradations of the compensating force. Compensating springs with different spring forces can also be provided. The plate 22 with one or more bushings 23, one or more springs 24 and one or more pistons 25 can be disconnected and disassembled from the base 1 by loosening of one or more screws 22a and it is possible to substitute an other aggregate of the same kind with one spring or a set of springs differently dimensioned.

In the illustrated effective condition, the additional compensating spring 24 acts over the piston 25 on the upper part 9 and it assists the effect of compensation of the spring 17. The weight of an instrument provided with a determined aggregate can therefore be optimally compensated. If this additional aggregate is removed, the compensating spring force must be reduced accordingly. This takes place in that the upper part 9 is at first brought in its lower end position or approximately in this position by rotation of the lever 2. In this position, the threaded lower end 28a of the screw 28 lies at the threaded hole 31 and the head 29 of the screw is somewhat raised from its supporting shoulder in the hole 27 of the piston 25. The opening 30 in the upper part 9 is so dimensioned that at least the uppermost part provided with a slit of the screw 28 can enter in this opening. By means of a screw-driver, the screw 28 is screwed in the threaded hole 31 until it is griped in this hole. The piston 25 is then somewhat screwed downwards against the force of the compensating spring 24 and tken away from the upper part 9. The additional compensating spring 24 is thus rendered ineffective for all vertical positions of the upper part 9. If the additional compensating spring is to be rendered effective again, the upper part 9 is brought at least approximately in its lower end position and then the screw 28 is unscrewed from the threaded hole 31 by means of a screw-driver. The piston 25 is then liberated and it lies again with the force of the additional compensating spring 24 at the upper part 9 and it participates to the weight compensation. If many additional compensating springs are present, it is possible to render them effective or ineffective as described above.

If it is not known in advance how much and/or which additional compensating springs are required, one proceeds preferably in that at first all present compensating springs are rendered effective. Then, one checks if the upper part 9, resp. an instrument supported by it pressed manually upwards, springs back downwards, by the play in the mechanics, when let loose. Normally, that is when the load is not already maximum, the preceding is not the case. Additional compensating springs are then cut off until for the first time the above mentioned downwards spring back takes place so that the correct, optimum adjustment is reached. One seeks also always a not fully complete compensation in order for any play in the vertical adjustment to be avoided.

Other means can be provided for anchoring the piston 25 to the base 1. Instead of the screw 28 which can be screwed in a threaded hole 31, a similar rod could be provided at the lower end with a projecting pin perpendicular to the longitudinal axis of the rod this pin being, similarly to a bayonet catch, locked in the plate 22 by rotation in one direction and unlocked by a rotation in the reverse direction. Means can also be provided in order to lock the piston 25 to the bushing 23 which surrounds it. As an example, to this position could be provided a radially projecting pin which in the case of an effective additional compensating spring, would enter in a vertical slit of the bushing 23 and which would be introduced at the lower end of this vertical slit, by rotation from above, in a part of the slit directed in the peripheral direction. The piston could in each case be coupled by a small rotation with the associated bushing 23, in order to render ineffective the additional compensating spring. Instead of the piston 25, it could also be provided a disk over which the additional compensating spring 24 acts on the upper part 9 and in which the screw 31 or a corresponding coupling element is suspended. It would also be possible to foresee other coupling elements continuously anchored in the base part 1b, which would be introduced from above in order to couple the piston 25 with the base part 1b thus rendering ineffective the compensating spring 24.

In the example of execution and for practical purpose, the coupling screw 28 can be reached from above and it serves for anchoring the piston 25 to the base by screw connection. To the contrary, it would also be possible to screw to the piston a coupling screw capable to be reached from below.

The spring or springs must not necessarily act in the axis of motion of the part to be compensated. Thus, e.g. horizontally lying springs could act through appropriate gears to vertically moving parts, in which case, it would be advantageous to conduct the mutual coupling and uncoupling of the ends of the spring from the side of the stationary support of the spring or springs. The means for coupling, res. uncoupling of the ends of the springs can also be actuated from an arbitrary side, manually or with tools, whereby e.g. as the case may be, a pivotable coupling anchoring must be actuated through an angular gear.

We claim:

1. A supporting device for an instrument, more particularly an ophthalmological instrument, comprising a part adjustable in height and designed to support said instrument, means for adjusting the height of said part, adjustable compensating spring means acting on said part for compensating the weight of said part and of an instrument supported thereon, wherein said adjustable spring means comprises a first spring means continuously and invariably acting on said part and at least one additional compensating spring selectively acting on said part, coupling means being provided for rendering said additional compensating spring effective or ineffective in that its extremities are coupled together or uncoupled from each other respectively during operation by said coupling means.

2. Supporting device according to claim 1, characterized in that a piston or a plate are provided as coupling means which are capable to be coupled, resp. uncoupled by rotation of a bajonet catch, or in that there are provided displaceable locking means for said piston, said plate or directly said spring.

3. Supporting device according to claim 1, characterized in that additional compensating springs of different spring forces are provided.

4. A supporting device according to claim 1, wherein said means for adjusting the height of said part is designed to bring said part into a lower end position wherein said coupling means are operable to couple or uncouple said additional compensating spring.

5. Supporting device according to claim 1 having a base, characterized in that the end which acts on said height adjustable part is capable to be coupled, resp. uncoupled from a base of the supporting device.

6. Supporting device according to claim 5, characterized in that said additional compensating spring is traversed by said coupling means capable to be coupled with the base.

7. Support device according to claim 1, characterized in that a compensating spring or a set of compensating springs is exchangeably mounted.

8. Supporting device according to claim 7 having a base, characterized in that said compensating spring or springs is, resp. are supported on a plate which is detachably connected with the said base, e.g. screwed.

9. Supporting device according to claim 1, characterized in that said additional compensating spring acts over a piston or a plate onto said height adjustable part.

10. Supporting device according to claim 9, characterized in that said coupling means is loosely suspended in said piston or said plate.

11. Supporting device according to claim 9, characterized in that said piston or said plate and said additional compensating spring are provided in a guiding bushing.

12. A supporting device for an instrument, more particularly an ophthalmological instrument, comprising a part adjustable in height and designed to support said instrument, a spindle and nut for fine-adjusting the height of said part, adjustable compensating spring means acting on said part for compensating the weight of said part and of an instrument supported thereon, wherein said adjustable spring means comprises a first spring means continuously and invariably acting on said part and at least one additional compensating selectively acting on said spring, coupling means being provided for rendering said additional compensating spring effective or ineffective in that its extremities are coupled together or uncoupled from each other respectively, said spindle and nut being adapted to bring said part into a lower end position wherein said coupling means are operable to couple or uncouple said additional compensating spring.

13. A supporting device for supporting an instrument, the supporting device comprising:
   a base;
   an upper part movable relative to the base;
   a first spring having first and second ends, the first end of the first spring being in contact with the base and the second end of the first spring pressing against the upper part;
   a spring biased piston assembly including a piston, movable relative to the base;
   a second spring, the second spring biasing the piston toward the upper part;
   a coupling selectively connectable to the base, the coupling including a portion which limits movement of the piston toward the upper part such that when the coupling is fixed to the base, the piston is held away from the upper part and when the coupling is disconnected from the base, the piston is biased against the upper part by the second spring.

14. The device of claim 13, further comprising a height adjusting assembly for selectively raising or lowering said upper part.

* * * * *